United States Patent [19]

Degner et al.

[11] Patent Number: 4,699,698
[45] Date of Patent: Oct. 13, 1987

[54] PREPARATION OF BENZOIC ACID ORTHO-ESTERS AND NOVEL COMPOUNDS OF THIS TYPE

[75] Inventors: Dieter Degner, Dannstadt-Schauernheim; Eberhard Steckhan, Meckenheim, both of Fed. Rep. of Germany

[73] Assignee: BASF Aktiengesellschaft, Ludwigshafen, Fed. Rep. of Germany

[21] Appl. No.: 895,171

[22] Filed: Aug. 11, 1986

[30] Foreign Application Priority Data

Aug. 14, 1985 [DE] Fed. Rep. of Germany ....... 3529074

[51] Int. Cl.⁴ ............................................. C25C 1/00
[52] U.S. Cl. ................................................. 204/59 R
[58] Field of Search ...................................... 204/59 R

[56] References Cited

U.S. PATENT DOCUMENTS

| | | | |
|---|---|---|---|
| 4,284,825 | 8/1981 | Degner et al. | 568/592 |
| 4,539,081 | 9/1985 | Degner et al. | 204/78 |
| 4,588,482 | 5/1986 | Degner | 204/59 R |
| 4,612,092 | 9/1986 | Degner et al. | 204/59 R |

FOREIGN PATENT DOCUMENTS 0129795 1/1985 European Pat. Off. .
0179289 4/1986 European Pat. Off. .

OTHER PUBLICATIONS

International Journal of Methods in Synthetic Organic Chemistry, Nr. 4, Apr. 1978, pp. 283–284, J. W. Scheeren et al.

J. Chem. Soc. Perkin I (1978), pp. 708–715.

*Primary Examiner*—R. L. Andrews
*Attorney, Agent, or Firm*—John H. Shurtleff

[57] ABSTRACT

Preparation of aromatic carboxylic acid ortho-esters of the formula I

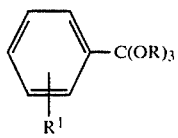

where R is $C_1$-$C_4$-alkyl and $R^1$ is H, halogen, alkyl, aryl, heteroaryl, alkoxy, aryloxy, acyl, acyloxy or CN, by electro-oxidizing benzene derivatives of the formula II

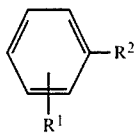

where $R^2$ is $CH_3$ or $CH(OR_2)$, in the presence of an alcohol ROH, a halogenated triarylamine compound and a base, and novel ortho-trialkyl 4-tert-butoxybenzoates, where alkyl is of 1 to 4 carbon atoms.

Ortho-trialkyl 4-tert-butoxybenzoates are scents and are also used to prepared p-hydroxybenzoic acid esters.

6 Claims, No Drawings

PREPARATION OF BENZOIC ACID ORTHO-ESTERS AND NOVEL COMPOUNDS OF THIS TYPE

The invention relates to a process for the preparation of benzoic acid ortho-esters by electro-oxidizing benzaldehyde dialkylacetals and/or toluene derivatives, and to novel ortho-trialkyl 4-tert-butoxybenzoates.

It is known from J. Chem. Soc. Perkin I (1978), 708–715 and German Pat. No. 2,848,397 that toluenes may be selectively converted to the corresponding benzaldehyde dimethylacetals by anodic oxidation in the presence of methanol. However, electrochemical oxidation of benzaldehyde dialkylacetals to the corresponding ortho-esters takes place with only very low selectivity even when using a very high excess of current.

It is the object of the invention to provide a process whereby unsubstituted or substituted ortho-trialkyl benzoates may be prepared with high selectivity.

We have found that this object is achieved and that aromatic carboxylic acid ortho-esters of the general formula I.

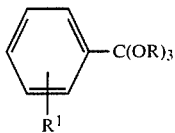

where R is alkyl of 1 to 4 carbon atoms and $R^1$ is hydrogen, halogen, alkyl, aryl, heteroaryl, alkoxy, aryloxy, acyl, acyloxy or cyano, may be prepared particularly advantageously when a benzene derivative of the general formula II

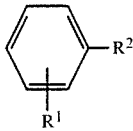

where $R^2$ is methyl or a radical of the formula —CH(OR)$_2$, is electrolyzed in the presence of
(a) an alcohol of the formula ROH,
(b) a triarylamine compound of the general formula III

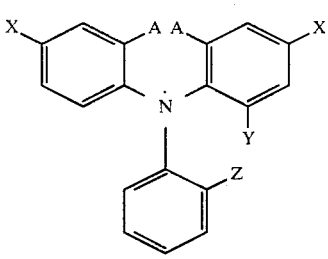

where each A is hydrogen or the two A together are a single bond, X is halogen, H$_3$COC—, NO$_2$— or NC—, Y is hydrogen, —NO$_2$ or CH$_3$CO— or halogen and Z is hydrogen, NO$_2$— or halogen and
(c) a base.

In the benzaldehyde dialkylacetals and the toluene derivatives of the formula II, R is alkyl of 1 to 4 carbon atoms, preferably methyl or ethyl. $R^1$ may be hydrogen or branched or unbranched alkyl, for example of 1 to 10, especially of 1 to 6, carbon atoms. Alkoxy groups $R^1$ are advantageously of 1 to 6 carbon atoms, eg. methoxy or ethoxy. Aryl and aryloxy groups $R^1$ are eg., phenyl and phenoxy. Acyl and acyloxy groups $R^1$ are, eg., —CO—CH$_3$ or —COOCH$_3$. Heteroaryl radicals $R^1$ are, eg., 5- or 6-membered heteroaromatics with 1 or 2 heteroatoms, such as nitrogen, oxygen or sulfur. $R^1$ may also be halogen, preferably chlorine or bromine, or cyano CN. The radical $R^1$ is in the meta-, ortho- or, preferably, para-position.

Examples of preferred starting materials of the formula II are benzaldehyde dimethylacetal, benzaldehyde diethylacetal, 4-methylbenzaldehyde dimethylacetal, 4-tert-butylbenzaldehyde dimethylacetal, 4-tert-butylbenzaldehyde dimethylacetal, 4-tert-butoxy-benzaldehyde dimethylacetal, 4-methoxybenzaldehyde dimethylacetal, 4-bromobenzaldehyde dimethylacetal, 4-chlorobenzaldehyde dimethylacetal, p-xylene and 4-tert-butyltoluene.

Alkanols of the formula ROH, where R has the above meaning, are, eg. ethanol, propanol, isopropanol, butanol, isobutanol and, preferably, methanol.

Triarylamine compounds of the formula III are compounds of the structure

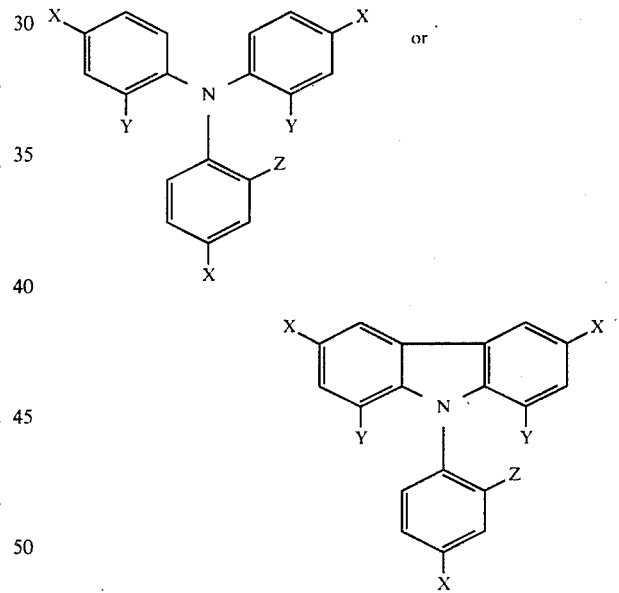

in which the halogen atoms are, eg., F, CL or Br. Examples of compounds of the formula III are tris-(4-bromophenyl)-amine, bis-(4-bromophenyl)-(2,4-dibromophenyl)-amine, bis-(2,4-dibromophenyl)-4-bromophenylamine, tris-(2,4-dibromophenyl)-amine, tris-(4-chlorophenyl)-amine, bis-(4-chlorophenyl)-(2,4-dichlorophenyl)-amine, bis-(2,4-dichlorophenyl)-(4-chlorophenyl)-amine and tris-(2,4-dichlorophenyl)-amine, of which tris-(2,4-dibromophenyl)-amine and tris-(2,4-dichlorophenyl)-amine are preferred.

Suitable bases are alkali metal and alkaline earth metal carbonates and bicarbonates, eg. LiCO$_3$, Na$_2$CO$_3$, NaHCO$_3$, K$_2$CO$_3$, KHCO$_3$ or MgCO$_3$. Preferred bases are alkali metal and alkaline earth metal hydroxides, eg. LiOH and especially NaOH, KOH and Mg(OH)$_2$. Particularly preferred bases are alcoholates of the general formula IV

Me(OR)$_x$            IV where Me is an alkali metal or alkaline earth metal, x is 1 or 2 and R is alkyl of 1 to 4 carbon atoms, for example NaOCH$_3$, NaOC$_2$H$_5$ or KOCH$_3$.

The conductive salts conventionally used in organic electrochemistry, eg. salts of tetrafluoboric acid, salts of alkyl sulfonic or aryl sulfonic acids, salts of alkylsulfuric acids and salts of perchloric acid, are added to the electrolyte. To increase the solubility of the electron transfer agent, cosolvents may be added to the electrolyte. Examples of suitable cosolvents are halohydrocarbons, eg. methylene chloride, dichloroethane, 1,2-dichloropropane, and nitriles, eg. acetonitrile. The cosolvents are added to the alcohol in, for example, amounts of up to 60 parts by weight per 100 parts by weight of alkanol.

The process according to the invention does not require any special electrolysis cell. Preferably, a non-partitioned continuous-flow well is employed. The anodes may consist of any conventional anode materials which are stable under the conditions of the electrolysis, such as noble metals, eg. gold or platinum. The use of graphite and vitreous carbon is preferred. Suitable cathode materials include graphite, iron, steel, nickel and noble metals, such as platinum.

The electrolyte employed in the electro-oxidation may for example have the following composition:
1-70% by weight of starting compound of the formula II,
30-96% by weight of alkanol, with or without cosolvent,
0.5-5% be weight of triarylamine compound of the formula III,
0.5-4% by weight of conductive salt and
0.05-3% by weight of base.

Electrolysis is carried out at current densities of 0.25-10 A/dm$^2$, advantageously 0.25-5 A/dm$^2$, preferably 0.5-3 A/dm$^2$. The charge employed is 2.5-25, preferably 3-20, F per mole of starting material.

An upper limit on the electrolysis temperature is imposed by the boiling point of the alkanol or of the cosolvent. Electrolysis is advantageously carried out at, for example, 10-5° C. below the boiling point of the electrolyte. When methanol is used, electrolysis is carried out at, for example,, up to 60° C., preferably at 20°-60° C. We have found, surprisingly, that the process according to the invention offers the possibility of very high conversion of the starting compounds of the formula II without significant deterioration in the selectivity of the electro-oxidation. The process may be carried out batchwise or continuously.

The electrolysis product is worked up by methods known per se, advantageously by distillation. Excess alkanol and any cosolvent employed are distilled off first. The conductive salt and triarylamine compound are filtered off and the benzoic acid ortho-ester purified by, for example, distillation. The alkanol, cosolvent, conductive salt and triarylamine compound as well as unconverted compound of the formula II may be recycled to the electrolysis. We have found no significant loss of triarylamine compound even after 2,500 regenerative cycles.

In carrying out the process we have found that the electro-oxidation can be carried out over a lengthy period without encountering electrode problems or deterioration of the selectivity of the electro-oxidation. This is remarkable since the industrial implementation of an organic electrolysis is often hampered by the performance of the electrodes which tend to acquire an extremely undesirable coating, especially if the electrolyte is being recycled.

The benzoic acid ortho-esters obtainable by the process according to the invention are used as scents. Ortho-trimethyl and ortho-triethyl 4-tert-butoxybenzoate have very interesting camphor-like and eugenol-like odors. They are also used as starting materials for the preparation of p-hydroxybenzoic acid esters, which are employed as foodstuff stabilizers.

EXAMPLE 1

Electrosynthesis of ortho-trimethyl 4-tert-butoxybenzoate I/1

Cell: unpartitioned cell with 9 electrodes
Anode: graphite
Electrolyte:
  894 g (33.0% by weight of 4-tert-butoxybenzaldehyde dimethylacetal II/1
  8.9 g (0.33% by weight) of tris-(2,4-dibromophenyl)-amine,
  8.9 g (0.33% by weight) of KSO$_3$C$_6$H$_5$,
  9.2 g (0.34% by weight) of NaOCH$_3$,
  1,787.2 g (66% by weight) of CH$_3$OH,
Cathode: graphite
Current density: 3.3 A/dm$^2$ Electrolysis with 3.4 F/mole of 4-tert-butoxybenzaldehyde dimethylacetal II/1, Temperature: 22°-24° C.,
Flow rate through cell: 200 l/h,
Working up:
  After completion of the electrolysis, CH$_3$OH was distilled off, the precipitated salt was filtered off and the residue was subjected to fractional distillation at 4 mbar pressure at the top. The main fraction distilled at 140° C. (temperature at the top). 137.3 g of 4-tert-butoxybenzaldehyde dimethylacetal II/1, 473.9 g of ortho-trimethyl 4-tert-butoxybenzoate I/1 and 44.6 g of methyl 4-tert-butoxybenzoate were obtained.
Result:
  Conversion of 4-tert-butoxybenzaldehyde dimethylacetal II/1: 85%
  Yield of ortho-trimethyl 4-tert-butoxybenzoate I/1: 47%
  Selectivity in respect of ortho-trimethyl 4-tert-butoxybenzoate I/1: 55%.

EXAMPLE 2

Electrosynthesis of ortho-trimethyl 4-methoxybenzoate I/2

Cell: unpartitioned cell with 11 electrodes,
Anode: graphite
Electrolyte:
  869 g (32.2% by weight) of 4-methoxybenzaldehyde dimethyl acetal II/2
  9.2 g (0.34% by weight) of tris-(2,4-dibromophenyl)-amine,
  9.2 g (0.34% by weight) of KSO$_3$C$_6$H$_5$,
  9.2 g (0.34% by weight) of NaOCH$_3$,
  1,782 g (66.78% by weight) of CH$_3$OH
Cathode: graphite
Current density: 2 A/dm$^2$ Electrolysis with 6 F/mole of 4-methoxybenzaldehyde dimethylacetal II/2

Temperature: 33°–36° C.
Cell flow rate: 200 l/h
Working up:
  Similar to Example 1. The fractional distillation was carried out with the following conditions at the top: 2 mbar pressure, 90°–150° C. 67 g of 4-methoxybenzaldehyde dimethylacetal II/2, 492 g of ortho-trimethyl 4-methoxybenzoate I/2 and 135 g of methyl 4-methoxybenzoate were obtained.
Result:
  Conversion of 4-methoxybenzaldehyde dimethylacetal II/2: 92%
  Yield of ortho-trimethyl 4-methoxybenzoate I/2: 49%
  Selectivity in respect of ortho-trimethyl 4-methoxybenzoate I/2: 53%.

EXAMPLE 3

Electrosynthesis of ortho-trimethyl 4-methylbenzoate I/3

Cell: unpartitioned cell wtih 11 electrodes,
Anode: graphite
Electrolyte:
  894 g (33.1% by weight) of 4-methylbenzaldehyde dimethylacetal II/3
  8.9 g (0.33% by weight) of tris-(2,4-dibromophenyl)-amine,
  8.9 g (0.33% by weight) of $KSO_3C_6H_5$
  8.9 g (0.33% by weight) of $NaOCH_3$
  1,780.2 g (65.91% by weight) of $CH_3OH$,
Cathode: graphite,
Current density: 2 A/dm$^2$ Electrolysis with 5.8 F/mole of 4-methylbenzaldehyde dimethylacetal II/3

Temperature: 33° C.
Cell flow rate: 200 l/h,
Working up:
  Similar to Example 1. The fractional distilation was carried out with the following conditions at the top: 2 mbar pressure, 70°–150° C. 230.3 g 4-methylbenzaldehyde dimethylacetal II/3, 240.1 g of ortho-trimethyl 4-methylbenzoate I/3, 81.1 g of methyl 4-methylbenzoate, 43.1 g of 4-methoxymethylbenzaldehyde dimethylacetal and 63.3 g of terephthalaldehyde di-dimethylacetal were obtained.
Result:
  Conversion of 4-methylbenzaldehyde dimethylacetal II/3: 74%
  Yield of ortho-trimethyl 4-methylbenzoate I/3: 23%,
  Selectivity in respect of ortho-trimethyl 4-methylbenzoate I/3: 31%.

EXAMPLE 4

Electrosynthesis of ortho-trimethyl 4-methylbenzoate I/3

Cell: unpartitioned cell with 2 electrodes
Anode: vitreous carbon
Electrolyte:
  1.66 g (1.66% by weight) of 4-methylbenzaldehyde dimethylacetal II/3,
  0.72 g (0.72% by weight) of tris-(2,4-dibromophenyl)-amine,
  1.6 g (1.6% by weight) of $LiCLO_4$,
  0.16 g (0.16% by weight) of $NaOCH_3$
  52.2 g (52.1% by weight) of $CH_3OH$
  43.8 g (43.7% by weight) of $CH_2Cl_2$
Cathode: platinum
Current density: 0.5–1.0 A/dm$^2$ Electrolysis with 15.6 F/mole of 4-methylbenzaldehyde dimethylacetal II/3

Temperature: 30° C.
Working up:
  The electrolysis solution was concentrated to half its volume, 20 ml of 5% strength $Na_2CO_3$ solution were added, and the mixture was extracted with pentane. The pentane solution was dried over $MgSO_4$, the solvent was separated off and the residue was purified by distillation. 0.166 g of 4-methylbenzaldehyde dimethylacetal II/3, 1.52 g of ortho-trimethyl 4-methylbenzoate I/3 and 0.16 g of 1-(dimethoxymethyl)-1,4-dimethoxy-4-methyl-cyclohexa-2,5-diene were obtained.
Result:
Conversion of 4-methylbenzaldehyde dimethylacetal II/3: 90%
  Yield of ortho-trimethyl 4-methylbenzoate I/3: 78%
  Selectivity in respect of ortho-trimethyl 4-methylbenzoate I/3: 87%.

EXAMPLE 5

Electrosynthesis of orthoo-trimethyl benzoate I/4

Cell: unpartitioned cell with 2 electrodes,
Anode: vitreous carbon
Electrolyte:
  1.53 g (1.53% by weight) of benzaldehyde dimethylacetal II/4,
  0.72 g (0.72% by weight) of tris-(2,4-dibromophenyl)-amine,
  1.6 g (1.6% by weight) of $LiClO_4$,
  0.16 g (0.16% by weight) of $NaOCH_3$,
  52.2 g (52.2% by weight) of $CH_3OH$,
  43.8 g (43.8% by weight) of $CH_2Cl_2$.
Cathode: platinum,
Current density: 0.5–1.0 A/dm$^2$ Electrolysis with 15.5 F/mole of benzaldehyde dimethylacetal II/4, Temperature: 30° C.
Working up:
  similar to Example 4. 0.055 g of benzaldehyde dimethylacetal II/4, 0.161 g of methyl benzoate and 1.508 g of ortho-trimethyl benzoate were obtained.
Result:
  Conversion of benzaldehyde dimethylacetal II/4: 96.4%
  Yield of ortho-trimethyl benzoate I/4: 82.5%
  Selectivity in respect of ortho-trimethyl benzoate I/4: 85.6%

EXAMPLE 6

Electrosynthesis of ortho-trimethyl 4-chlorobenzoate I/5

Cell: unpartitioned cell with 2 electrodes,
Anode: vitreous carbon,

Electrolyte:
  1.87 g (1.86% by weight) of 4-chlorobenzaldehyde dimethylacetal II/5,
  0.72 g (0.72% by weight) of tris-(2,4-dibromophenyl)-amine,
  1.6 g (1.6% by weight) of LiClo$_4$,
  0.16 g (0.16% by weight) of NaOCH$_3$,
  52.2 g ( 52.0% by weight) of CH$_3$OH,
  43.8 g (43.6% by weight) of CH$_2$Cl$_2$,
Cathode: platinum,
Current density: 0.5–1.0 A/dm$^2$, Electrolysis with 25.9 F/mole of 4-chlorobenzaldehyde dimethylacetal II/5, Working up:
  similar to Example 4. 0.19 g of 4-chlorobenzaldehyde dimethylacetal II/5, 0.197 g of methyl 4-chlorobenzoate and 1.636 g of ortho-trimethyl 4-chlorobenzoate I/5 were obtained.
Result:
  Conversion of 4-chlorobenzaldehyde dimethylacetal II/5: 89.7%
  Yield of ortho-trimethyl 4-chlorobenzoate I/5: 75.5%
  Selectivity in respect ortho-trimethyl 4-chlorobenzoate I/5: 84%.

EXAMPLE 7

Electrosynthesis of ortho-trimethyl 4-bromobenzoate I/6

Cell: unpartitioned cell with 2 electrodes,
Anode: vitreous carbon,
Electrolyte:
  2.36 g (2.34% by weight) of 4-bromobenzaldehyde dimethylacetal II/6,
  0.72 g (0.72% by weight) of tris-(2,4-dibromophenyl)-amine,
  1.6 g (1.6% by weight) of LiClO$_4$,
  0.16 g (0.16% by weight) of NaOCH$_3$,
  52.2 g (51.8% by weight) of CH$_3$OH,
  43.8 g (43.4% by weight) of CH$_2$Cl$_2$,
Cathode: platinum,
Current density: 0.5 to 1.0 A/dm$^2$, Electrolysis with 18.2 F/mole of 4-bromobenzaldehyde dimethylacetal II/6, Working up:
  Similar to Example 4. 0.2 g of 4-bromobenzaldehyde dimethylacetal II/6, 0.078 g of methyl 4-bromobenzoate and 2.16 g of ortho-trimethyl 4-bromobenzoate I/6 were obtained.
Result:
  Conversion of 4-bromobenzaldehyde dimethylacetal II/6: 92%
  Yield of ortho-trimethyl 4-bromobenzoate I/6: 87.5%
  Selectivity in respect of ortho-trimethyl 4-bromobenzoate I/6: 95%.

EXAMPLE 8

Electrosynthesis of ortho-trimethyl 4-tert-butylbenzoate I/7

Cell: unpartitioned cell with 2 electrodes,
Anode: vitreous carbon,
Electrolyte:
  2.09 g (2.08% by weight) of 4-tert-butylbenzaldehyde dimethylacetal II/7,
  0.72 g (0.72% by weight) of tris-(2,4-dibromophenyl)-amine,
  1.6 g (1.6% by weight) of LiClO$_4$,
  0.16 g (0.16% by weight) of NaOCH$_3$,
  52.2 g (51.9% by weight) of CH$_3$OH,
  43.8 g (43.55% by weight) of CH$_2$Cl$_2$,
Cathode: platinum,
Current density: 0.5–1.0 A/dm$^2$, Electrolysis with 12.9 F/mole of 4-tert-butylbenzaldehyde dimethylacetal II/7, Working up:
  Similar to Example 4. 0.125 g of methyl 4-tert butylbenzoate and 2.16 g of ortho-trimethyl 4-tert-butylbenzoate I/7 were obtained.
Result:
  Conversion of 4-tert-butylbenzaldehyde dimethylacetal II/7: 100%
  Yield of ortho-trimethyl 4-tert-butylbenzoate I/7: 90.4%
  Selectivity in respect of ortho-trimethyl 4-tert-butylbenzoate I/7: 90.4%.

EXAMPLE 9

Electrosynthesis of ortho-trimethyl 4-methoxybenzoate I/2

Cell: unpartitioned cell with 2 electrodes,
Anode: vitreous carbon,
Electrolyte:
  1.83 g (1.82% by weight) of 4-methoxybenzaldehyde dimethylacetal II/2
  0.72 g (0.72% by weight) of tris-(2,4-dibromophenyl)-amine,
  1.6 g (1.6% by weight) of LiClO$_4$,
  0.16 g (0.16% by weight) of NaOCH$_3$,
  52.2 g (52.0% by weight) of CH$_3$OH,
  43.8 g (43.7% by weight) of CH$_2$Cl$_2$,
Cathode: platinum,
Current density: 0.5–1.0 A/dm$^2$, Electrolysis with 12.4 F/mole of 4-methoxybenzaldehyde dimethylacetal II/2, Working up:
  Similar to Example 4. 0.22 g of methyl 4-methoxybenzoate and 1.67 g of ortho-trimethyl 4-methooxybenzoate I/2 were obtained.
Result:
  Conversion of 4-methoxybenzaldehyde dimethylacetal II/2: 100%,
  Yield of ortho-trimethyl 4-methoxybenzoate I/2: 78.3%,
  Selectivity in respect of ortho-trimethyl 4-methoxybenzoate I/3: 78.3%.

EXAMPLE 10

Electrosynthesis of ortho-trimethyl 4-tert-butoxybenzoate I/1

Cell: unpartitioned cell with 2 electrodes,
Anode: vitreous carbon,
Electrolyte:
  2.25 g (2.23% by weight) of 4-tert-butoxybenzaldehyde dimethylacetal II/1,
  0.72 g (0.72% by weight) of tris-(2,4-dibromophenyl)-amine,
  1.6 g (1.6% by weight) of LiClO$_4$,
  0.16 g (0.16% by weight) of NaOCH$_3$,
  52.2 g (51.8% by weight) of CH$_3$OH, 43.8 g (43.5% by weight) of $CH_2Cl_2$,
Cathode: platinum,
Current density: 0.5–1.0 $A/dm^2$, Electrolysis with 13.5 F/mole of 4-tert-butoxybenzaldehyde dimethylacetal II/1, Working up:

Similar to Example 4. 0.09 g of 4-tert-butoxybenzaldehyde dimethylacetal II/1, 0.42 g of methyl 4-tert-butoxybenzoate and 2.28 g of ortho-trimethyl 4-tert-butoxybenzoate I/1 were obtained.

Result:

Conversion of 4-tert-butoxybenzaldehyde dimethylacetal II/1: 96%,

Yield of ortho-trimethyl 4-tert-butoxybenzoate I/1: 89.4%,

Selectivity in respect of ortho-trimethyl 4-tert-butoxybenzoate I/1: 93%.

EXAMPLE 11

Electrosynthesis of ortho-trimethyl 4-tert-butylbenzoate I/9

Cell: unpartitioned cell with 2 electrodes,
Anode: vitreous carbon,
Electrolyte:

1.49 g (1.46% by weight) of 4-tert-butyltoluene II/9, 0.72 g (0.70% by weight) of tris-(2,4-dibromophenyl)amine, 2.1 g (2.06% by weight) of $Na_2CO_3$, 52.2 g (51.1% by weight) of $CH_3OH$, 43.8 g (42.9% by weight) of $CH_2Cl_2$, 1.83 g (1.79% by weight) of $NaClO_4$, Cathode: platinum, Current density: 0.5–1.0 $A/dm^2$, Electrolysis with 20 F/mole of 4-tert-butyltoluene II/9, Working up:

Similar to Example 4. 0.2 g of methyl 4-tert-butylbenzoate, 0.178 g of 4-tert-butylbenzyl methyl ether, 0.06 g of 4-tert-butylbenzaldehyde dimethylacetal, 0.74 g of ortho-trimethyl 4-tert-butylbenzoate I/3 and 0.58 g of 4-tert-butyltoluene II/9 were obtained.

Result:

Conversion of 4-tert-butylbenzoate I/9: 31%,

Selectivity in respect of ortho-trimethyl 4-tert-butylbenzoate I/9: 51%.

We claim:

1. A process for the preparation of aromatic carboxylic acid ortho esters of the formula

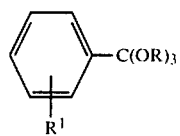

where R is alkyl of 1 to 4 carbon atoms and $R^1$ is hydrogen, halogen, alkyl, aryl, heteroaryl, alkoxy, aryloxy, acyl, acyloxy or cyano, which process comprises:
electrolyzing a benzene derivative of the formula

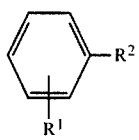

where $R^2$ is methyl or a radical of the formula $-CH(OR)_2$, R and $R^1$ having the meanings given above, in the presence of
(a) an alcohol of the formula ROH,
(b) a triarylamine compound of the formula

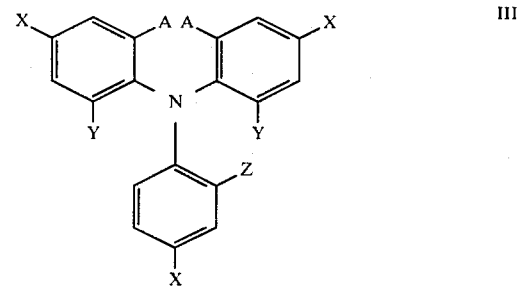

where each A is hydrogen or, taken together, form a single bond joining their respective benzene rings, X is halogen, $H_3COC-$, $NO_2-$ or $NC-$, Y is hydrogen, $-NO_2$ or $CH_3CO-$ or halogen and Z is hydrogen, $NO_2-$ or halogen, and
(c) a base.

2. A process as claimed in claim 1, wherein methanol is used as the alcohol.

3. A process as claimed in claim 1, wherein tris-2,4-dibromophenyl)-amine or tris-(2,4-dichlorophenyl)-amine is used as the triarylamine compound.

4. A process as claimed in claim 1, wherein the base used is an alcoholate of the formula IV $$Me(OR)_x \qquad \text{IV.}$$

where Me is an alkali metal or an alkaline earth metal, x is 1 or 2 and R is alkyl of 1 to 4 carbon atoms.

5. A process as claimed in claim 1, wherein the electrolyte used contains 1–70% by weight of benzaldehyde dialkylacetal of the formula II, 30–96% by weight of alkanol with or without cosolvent, 0.5–5.0% by weight of triarylamine compound, 0.05–3.0% by weight of base and 0.5–4.0% by weight of conductive salt.

6. A process as claimed in claim 1, wherein electrolysis is carried out with a current density of 0.25–10.0 $A/dm^2$.

* * * * *